United States Patent [19]

Yamamoto et al.

[11] Patent Number: 5,434,082
[45] Date of Patent: Jul. 18, 1995

[54] EARLY DIAGNOSIS OF MASTITIS OR GARGET

[75] Inventors: Hideo Yamamoto, Toride; Eiji Furukawa; Hiromoto Asai, both of Nagoya; Masayasu Kurono, Mie; Kiichi Sawai, Funabashi, all of Japan

[73] Assignee: Sanwa Kagaku Kenkyusho Co., Ltd, Nagoya, Japan

[21] Appl. No.: 1,413

[22] Filed: Jan. 7, 1993

Related U.S. Application Data

[63] Continuation of Ser. No. 737,081, Jul. 29, 1991, abandoned.

[30] Foreign Application Priority Data

Aug. 6, 1990 [JP] Japan .................................. 2-207828

[51] Int. Cl.⁶ .......................... C12Q 1/00; C12Q 1/25; C07C 49/00
[52] U.S. Cl. ......................................... 436/23; 435/4; 435/26; 435/28; 436/22
[58] Field of Search ................. 435/4, 26, 28; 436/23, 436/22

[56] References Cited

FOREIGN PATENT DOCUMENTS

| 0097506 | 1/1984 | European Pat. Off. . |
|---|---|---|
| 0226427 | 6/1987 | European Pat. Off. . |
| 0226427B1 | 7/1991 | European Pat. Off. . |
| 62-135771 | 6/1987 | Japan . |
| 0226427B1 | 8/1986 | United Kingdom . |

OTHER PUBLICATIONS

Shoop, et al. Am. J. Vet. Res. vol. 45, No. 10, pp. 1944–1946.
Herdt et al Am J Vet Res vol. 42, No. 3 (1981) pp. 503–506.
"Clinical Diagnosis and Management by Laboratory Methods", 17th Edition, pp. 412–413, published by W. B. Saunders Company, 1984.
Patent Abstract of Japan, Vo. 11, No. 362 (P-640) (2809), 26 Nov. 1987.

*Primary Examiner*—William H. Beisner
*Assistant Examiner*—Jane Williams
*Attorney, Agent, or Firm*—Armstrong, Westerman, Hattori, McLeland & Naughton

[57] ABSTRACT

Early diagnosis of mastitis or garget is carried out by measuring the concentration of 3-hydroxybutyric acid in milk. Used to this end is a reagent reacting with 3-hydroxybutyric acid to show a color at a concentration of 100 μmol/l or higher.

2 Claims, 1 Drawing Sheet

EARLY DIAGNOSIS OF MASTITIS OR GARGET

This application is a continuation of application Ser. No. 07/737,081 filed Jul. 29, 1991, now abandoned.

BACKGROUND OF THE INVENTION

1. Field of the Invention

This invention relates to early diagnosis of mastitis or garget by measuring the concentration of 3-hydroxybutyric acid (3-OHBA for short) in the milk of mammals.

2. Prior Art

The concentration of 3-OHBA in milk, which is less than 100 $\mu$mol/l for normal cattle, is well known to increase drastically in the case of ketosis that is the dysbolism of lipid and carbohydrates. Reagents for taking an expeditious measurement of the concentration of 3-OHBA are now commercially sold by Sanwa Co., Ltd. ("Lactest") and other firms.

Various conditions have been studied by the inventors to uncover the association of all ketone bodies (acetone, acetoacetic acid and 3-OHBAs) in such body fluids as urine and blood with the quality of mammalian milk and the health condition of livestock, as already reported (see JP-A-62-135771 specification). It has been reported that ketosis conditions are induced not only by diabetes but by various forms of shock, organopathies such as hepatitis, infectious diseases and drug (e.g. salicylic acid) poisoning as well ("Clinical Diagnosis and Management by Laboratory Methods", 17th Ed., pp. 412–413, published by W. B. Saunders Co. (1984).

Reagents for the separation and quantitative determination of a ketone body recently developed by Sanwa Co., Ltd. and other firms are now being used not only for diagnosis of diabetes but also for measuring the degree of activity of cell mitochondria at the time of liver transplantation-determination of the degree of rejection after transplantation, or for other purposes.

However, never until now has there been any report about the association of ketosis with mastitis or garget; in other words, they have been considered to have nothing to do with each other. Nor has anything been reported about the association of a ketone body with mastitis or garget.

In general, early detection of mastitis during a period of human lactation is of vital significance in view of protecting infants and, at the same time, the mothers. Garget, which is a typical disease of dairy cattle that incurs serious economical losses, is a type of inflammation which attacks the mammary gland tissue and lactiferous duct mainly through bacterial infection, and inhibits the lactigenous function and exasperates permeation of the milk secreting cell membrane, thus producing unusual milk in which blood components are incorporated.

Dairy cattle produce a ketone body in the liver and digestive tracts after feed intake, which is then used as an energy source after oxidation in the heart, kidney, brain and other organs. In the mammae, however, the ketone body is used not only as an energy source but also for synthesis of short-chain fatty acids of milk components.

A cow with ketosis or having a high concentration of ketones in the blood is found to have decreases in the activity of peripheral lymphocytes and the number of T-lymphocytes, and this suggests that the cow has a great chance of suffering from garget due to a drop of immune responsibility.

In an initial stage of mastitis or garget, the affected mammary gland tissue (cells) is locally inflamed or broken on a small scale, and a part of the blood components is mixed with milk components in the lactiferous duct, aggregated lactiferous duct, lactiferous sinus and other regions, leading to the production of unusual milk.

Early diagnosis of mastitis or garget to measure to what extent the mammary cells are affected or broken involves measuring the content of chlorine in milk, counting somatic cells in milk, determining NAGase activity and the like. However, a problem with these procedures, which are all awkward to handle, is that they cannot be used for ordinary, expeditious detection.

In view of the above-mentioned problem, the present invention seeks to provide a process for early diagnosis of mastitis or garget, which makes it possible to easily learn whether or not the subject suffers from mastitis or garget during lactation or milking.

In order to achieve the above-mentioned object and with the fact that separation and quantitative determination of a ketone body can now be easily carried out in mind, the inventors have uncovered the correlation, so far not found, between 3-OHBA produced in milk and mastitis or garget. Thus, the inventors have accomplished this invention.

SUMMARY OF THE INVENTION

According to one aspect of this invention, there is provided a process for early diagnosis for mastitis or garget by measuring the concentration of 3-OHBA in milk.

According to another aspect of this invention, there is provided a process for early diagnosis of mastitis or garget, in which the concentrations of 3-OHBA in milk produced from a plurality of mammae are determined to find a difference between a plurality of measurements.

DETAILED EXPLANATION OF THE INVENTION

Figure 1:
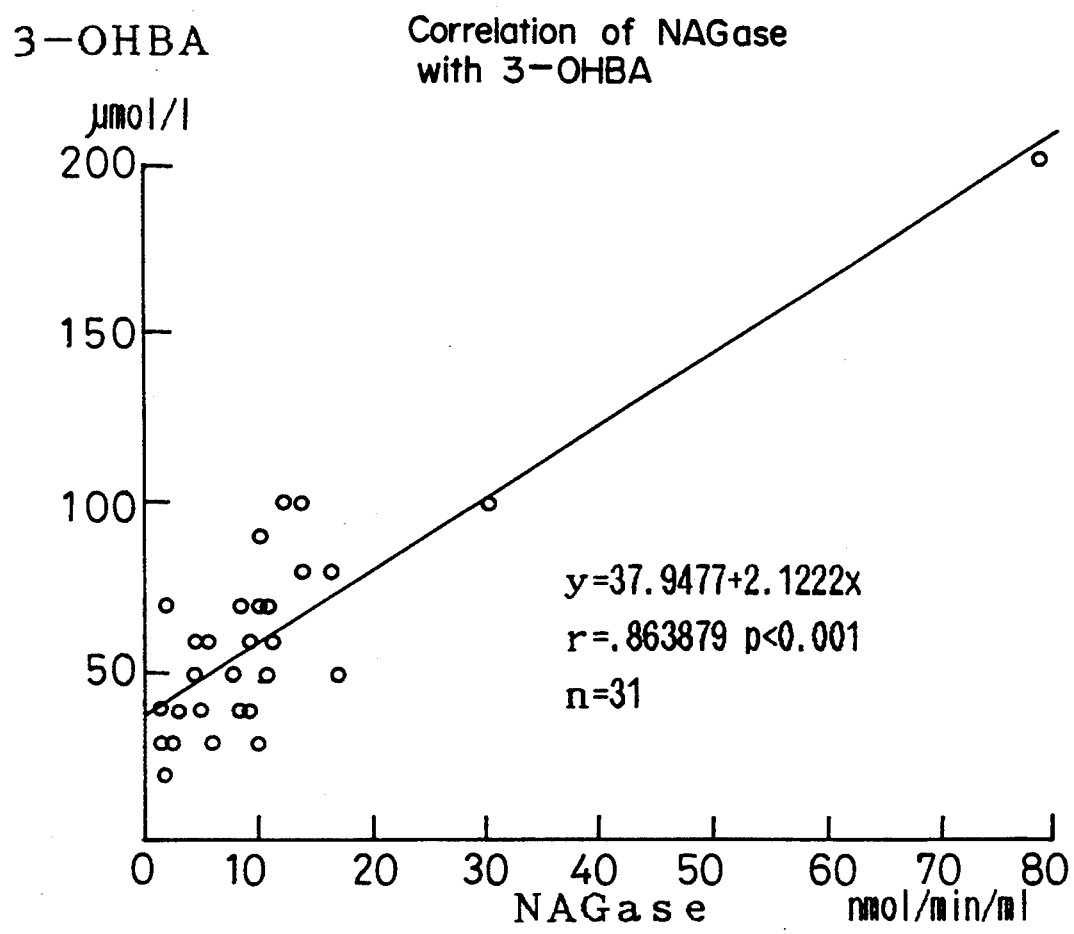
FIG. 1 is a graph showing the correlation between NAGase that is an index to mastitis or garget and 3-OHBA.

According to the results of experimentation made by the inventors, if the concentration or 3-OHBA in milk is equal to or more than 100 $\mu$mol/l it can then be diagnosed as mastitis or garget. A reagent, which can be colored when the concentration of 3-OHBA in milk exceeds 100 $\mu$mol/l may be used to this end.

Mastitis or garget is an inflammation of the mammary gland tissue or the lactiferous duct, which inhibits normal lactogenesis. This in turn hinders the normal synthesis of acetoacetic acid from 3-OHBA, which would be well achieved if the mammary gland tissue is in good condition. As a result, there is not only an increase in the amount of 3-OHBA transuding in milk, as is the case with ketosis, but also a serious increase in the amount of the transudation of the blood components, which is induced by cytoclasis. Thus, the concentration of 3-OHBA in milk comes to exceed 100 $\mu$mol/l.

In the case of ketosis in which the concentration of 3-OHBA in the blood is excessively high, there is an increase in the amount and hence concentration of that acid transuding in milk. Thus, the subject, if in good health condition, can be diagnosed as mastitis or garget when the amount of 3-OHBA transuding in the milk is found to increase. While ketosis causes an increase in the concentration of 3-OHBA in milk irrespective of what condition the mammae are in, mastitis or garget allows only the inflammed mamma to show an increase in the concentration of 3-OHBA in the milk. Thus, the subject can be diagnosed as mastitis or garget when a difference in the concentration of 3-OHBA between the affected and normal mammae is found to be higher than 50 μmol/l.

The present invention will now be explained specifically but not exclusively with reference to the following examples.

EXAMPLE 1

This example is provided to explain the correlation between the conventional diagnosis of mastitis or garget by the determination of NAGase activity and the present diagnosis.

The NAGase activity (N-acetyl-D-glucosaminidase) that is an index to what extent the mammary gland tissue is broken was assayed with the conventional procedure under the conditions provided by "A Guide To Treating Special Diseases And Wounds In Livestock" published by the National Agricultural Mutual Aid Association.

The subject is diagnosed as mastitis or garget when the NAGase activity exceeds 10 nmol/min/ml, and it is said that the higher the activity, the more serious the degree of inflammation.

The concentration of 3-OHBA, on the other hand, was measured with a test piece including a reagent layer impregnated with 25 μg of nicotinic acid amide adenine dinucleotide, 0.5 U of 3-OHBA dehydrogenase, 1.0 U of diaphorase and 25 μg of nitro blue tetrazolium ("Lactest" made by Sanwa Co., Ltd. ). Then, the concentration of 3-OHBA was determined by comparing a color developed by the dropwise addition of a milk sample to the reagent layer with a pre-prepared hue diagram.

As can be understood from the results set out in Table 1 and illustrated in FIG. 1, it has been found that the concentration of 3-OHBA correlates with the NAGase activity.

TABLE 1

| Sample Nos. | NAGase Activity (nmol/min/ml) | Concentration of 3-OHBA (μmol/l) |
|---|---|---|
| 1 | 9.199 | 40 |
| 2 | 9.965 | 90 |
| 3 | 8.383 | 70 |
| 4 | 4.934 | 40 |
| 5 | 13.650 | 100 |
| 6 | 5.523 | 60 |
| 7 | 4.647 | 60 |
| 8 | 4.646 | 50 |
| 9 | 2.914 | 40 |
| 10 | 17.070 | 50 |
| 11 | 2.339 | 30 |
| 12 | 1.833 | 20 |
| 13 | 11.910 | 100 |
| 14 | 1.814 | 30 |
| 15 | 1.484 | 40 |
| 16 | 1.712 | 70 |
| 17 | 10.060 | 30 |
| 18 | 7.720 | 50 |
| 19 | 9.926 | 70 |
| 20 | 4.955 | 40 |
| 21 | 9.579 | 60 |
| 22 | 78.520 | 200 |
| 23 | 10.810 | 50 |
| 24 | 8.531 | 40 |
| 25 | 6.083 | 30 |
| 26 | 10.770 | 50 |
| 27 | 13.740 | 80 |
| 28 | 16.460 | 80 |
| 29 | 10.710 | 10 |
| 30 | 11.120 | 60 |
| 31 | 29.930 | 100 |

Correlation between the values of NAGase activity found and the concentration of 3-OHBA in milk Number of cases 31
Coefficient of correlation r = 0.864
Regression curve y = 2.12X + 37.95

EXAMPLE 2

The same test piece as in Ex. 1 was used to determine whether or not cows suffered from garget and a difference in the concentration of 3-OHBA in the milk between the mammae. The results (in μmol/l) are reported in Table 2.

TABLE 2

| Cow Nos. | A (Concentration of 3-OHBA in the milk of the mammae with garget) | B (Concentration of 3-OHBA in the milk of the normal mammae) | | |
|---|---|---|---|---|
| 1 | 100 | 50 | 50 |  |
|   |     | 50 | 50 |  |
|   |     | 50 | 50 |  |
| 2 | 180 | 30 | 150 |  |
|   |     | 40 | 140 |  |
|   |     | 70 | 110 |  |
| 3 | 180 | 50 | 130 |  |
|   |     | 70 | 110 |  |
|   |     | 40 | 140 |  |
| 4 | 200 | 60 | 140 |  |
|   |     | 20 | 180 |  |
|   |     | 50 | 150 |  | t Assay: t value = −9.149, P value = 1.785 × $10^{-6}$

As mentioned above, this invention is efficacious for early detection and treatment of mastitis during a period of human lactation which is of vital significance in view of protecting infants and, at the same time, the mothers, and of garget which is a typical disease in dairy cattle.

What is claimed is:

1. A process for diagnosis of mastitis or garget in an early stage thereof in a mammal, comprising measuring the concentration of 3-hydroxybutyric acid in the milk of each of a plurality of mammae of the mammal to find a difference between said measured concentrations wherein said difference indicates that the mammal has mastitis or garget.

2. The process of claim 1 wherein said difference in said measured concentration is higher than 50 μmol/l.

* * * * *